US011324605B2

(12) United States Patent
De Villiers et al.

(10) Patent No.: US 11,324,605 B2
(45) Date of Patent: *May 10, 2022

(54) POSTERIOR PROSTHETIC INTERVERTEBRAL DISC

(71) Applicant: Simplify Medical Pty Ltd, Paddington (AU)

(72) Inventors: Malan De Villiers, Wapadrand (ZA); Neville Jansen, Waterkloof (ZA)

(73) Assignee: Simplify Medical Pty Ltd, Paddington (AU)

( * ) Notice: Subject to any disclaimer, the term of this patent is extended or adjusted under 35 U.S.C. 154(b) by 231 days.

This patent is subject to a terminal disclaimer.

(21) Appl. No.: 16/509,241

(22) Filed: Jul. 11, 2019

(65) Prior Publication Data
US 2019/0350721 A1    Nov. 21, 2019

Related U.S. Application Data

(60) Continuation of application No. 15/144,689, filed on May 2, 2016, now abandoned, which is a division of
(Continued)

(51) Int. Cl.
 *A61F 2/44* (2006.01)
 *A61F 2/46* (2006.01)
 *A61F 2/30* (2006.01)

(52) U.S. Cl.
 CPC ............ *A61F 2/4425* (2013.01); *A61F 2/442* (2013.01); *A61F 2/4611* (2013.01);
(Continued)

(58) Field of Classification Search
 CPC .. A61F 2002/30166; A61F 2002/30364; A61F 2002/30471; A61F 2002/30556;
(Continued)

(56) References Cited

U.S. PATENT DOCUMENTS 3,486,505 A    12/1969  Gordon
3,867,728 A     2/1975  Stubstad et al.
(Continued)

FOREIGN PATENT DOCUMENTS

DE    3023353 A1   4/1981
EP    0333990 A2   9/1989
(Continued)

OTHER PUBLICATIONS

"Office action dated May 1, 2017 for U.S. Appl. No. 15/144,689".
"Office action dated May 4, 2017 for U.S. Appl. No. 15/187,569".
"Office action dated Sep. 18, 2017 for U.S. Appl. No. 15/187,569".
Buttner-Janz, The Development of the Artificial Disc. Introduction, pp. 1-18, Library of Congress Catalogue No. 92-75582, ISBN 0-9635430-0-8 (1989).
(Continued)

*Primary Examiner* — Samuel S Hanna
(74) *Attorney, Agent, or Firm* — Hoffman Warnick LLC

(57) ABSTRACT

A prosthetic intervertebral disc is formed of first and second end plates sized and shaped to fit within an intervertebral space and to be implanted from the back of the patient, thereby decreasing the invasiveness of the procedure. The posterior approach provides for a smaller posterior surgical incision and avoids important blood vessels located anterior to the spine particularly for lumbar disc replacements. The first and second plates are each formed of first, second and third parts are arranged in a first configuration in which the parts are axially aligned to form a low profile device appropriate for insertion through the small opening available in the TLIF or PLIF approaches described above. The three parts of both of the plates rotate and translate with respect to one another in situ to a second configuration or a deployed configuration in which the parts are axially unaligned with each other to provide a maximum coverage of the vertebral end plates for a minimum of insertion profile. Upon deployment of the disc, a height of the disc is increased.

45 Claims, 5 Drawing Sheets

Related U.S. Application Data application No. 14/467,274, filed on Aug. 25, 2014, now Pat. No. 9,351,846, which is a division of application No. 12/504,042, filed on Jul. 16, 2009, now Pat. No. 8,845,730.

(60) Provisional application No. 61/081,952, filed on Jul. 18, 2008.

(52) U.S. Cl.
CPC ... *A61F 2/30965* (2013.01); *A61F 2002/3008* (2013.01); *A61F 2002/30166* (2013.01); *A61F 2002/30364* (2013.01); *A61F 2002/30471* (2013.01); *A61F 2002/30556* (2013.01); *A61F 2002/30579* (2013.01); *A61F 2002/30649* (2013.01); *A61F 2002/30662* (2013.01); *A61F 2002/30663* (2013.01); *A61F 2002/30841* (2013.01); *A61F 2002/30904* (2013.01); *A61F 2002/443* (2013.01); *A61F 2002/4415* (2013.01); *A61F 2220/0016* (2013.01); *A61F 2220/0033* (2013.01); *A61F 2220/0091* (2013.01); *A61F 2230/0028* (2013.01); *A61F 2250/0009* (2013.01); *A61F 2250/0098* (2013.01); *A61F 2310/00017* (2013.01); *A61F 2310/00023* (2013.01); *A61F 2310/00029* (2013.01); *A61F 2310/0088* (2013.01); *A61F 2310/00407* (2013.01); *A61F 2310/00796* (2013.01)

(58) Field of Classification Search
CPC .. A61F 2002/30579; A61F 2002/30649; A61F 2002/30662; A61F 2002/30663; A61F 2002/443; A61F 2220/0091; A61F 2250/0009; A61F 2/442; A61F 2/4425; A61F 2/4611
See application file for complete search history.

(56) References Cited

U.S. PATENT DOCUMENTS

| | | |
|---|---|---|
| 4,309,777 A | 1/1982 | Patil |
| 4,531,917 A | 7/1985 | Linkow, I et al. |
| 4,566,466 A | 1/1986 | Ripple et al. |
| 4,619,660 A | 10/1986 | Christiansen et al. |
| 4,673,407 A | 6/1987 | Martin |
| 4,759,766 A | 7/1988 | Buettner-Janz et al. |
| 4,759,769 A | 7/1988 | Hedman et al. |
| 4,834,757 A | 5/1989 | Brantigan |
| 4,863,477 A | 9/1989 | Monson |
| 4,904,261 A | 2/1990 | Dove et al. |
| 4,917,704 A | 4/1990 | Frey et al. |
| 4,932,969 A | 6/1990 | Frey et al. |
| 4,946,378 A | 8/1990 | Hirayama et al. |
| 4,997,432 A | 3/1991 | Keller et al. |
| 5,035,716 A | 7/1991 | Downey |
| 5,057,108 A | 10/1991 | Shetty et al. |
| 5,071,437 A | 12/1991 | Steffee |
| 5,122,130 A | 6/1992 | Keller |
| 5,195,526 A | 3/1993 | Michelson |
| 5,258,031 A | 11/1993 | Salib et al. |
| 5,282,861 A | 2/1994 | Kaplan |
| 5,314,477 A | 5/1994 | Marnay |
| 5,320,644 A | 6/1994 | Baumgartner |
| 5,370,697 A | 12/1994 | Baumgartner et al. |
| 5,394,457 A | 2/1995 | Leibinger et al. |
| 5,401,269 A | 3/1995 | Buttner-Janz et al. |
| 5,415,704 A | 5/1995 | Davidson |
| 5,458,642 A | 10/1995 | Beer et al. |
| 5,462,575 A | 10/1995 | Del Corso |
| 5,484,437 A | 1/1996 | Michelson |
| 5,489,307 A | 2/1996 | Kuslich et al. |
| 5,505,732 A | 4/1996 | Michelson |
| 5,507,816 A | 4/1996 | Bullivant |
| 5,534,030 A | 7/1996 | Navarro et al. |
| 5,556,431 A | 9/1996 | Büttner-Janz |
| 5,674,296 A | 10/1997 | Bryan et al. |
| 5,676,701 A | 10/1997 | Yuan et al. |
| 5,676,702 A | 10/1997 | Ratron |
| 5,683,465 A | 11/1997 | Shinn et al. |
| 5,702,450 A | 12/1997 | Bisserie |
| 5,709,683 A | 1/1998 | Bagby |
| 5,728,159 A | 3/1998 | Stroever et al. |
| 5,741,253 A | 4/1998 | Michelson |
| 5,776,198 A | 7/1998 | Rabbe et al. |
| 5,782,832 A | 7/1998 | Larsen et al. |
| 5,797,909 A | 8/1998 | Michelson |
| 5,824,094 A | 10/1998 | Serhan et al. |
| 5,865,846 A | 2/1999 | Bryan et al. |
| 5,865,848 A | 2/1999 | Baker |
| 5,888,226 A | 3/1999 | Rogozinski |
| 5,895,428 A | 4/1999 | Berry |
| 5,899,901 A | 5/1999 | Middleton |
| 5,899,911 A | 5/1999 | Carter |
| 5,928,284 A | 7/1999 | Mehdizadeh |
| 5,989,251 A | 11/1999 | Nichols |
| 5,989,291 A | 11/1999 | Ralph et al. |
| 6,001,130 A | 12/1999 | Bryan et al. |
| 6,019,792 A | 2/2000 | Cauthen |
| 6,022,376 A | 2/2000 | Assell et al. |
| 6,039,761 A | 3/2000 | Li et al. |
| 6,039,763 A | 3/2000 | Shelokov |
| 6,080,155 A | 6/2000 | Michelson |
| 6,083,228 A | 7/2000 | Michelson |
| 6,086,613 A | 7/2000 | Camino et al. |
| 6,096,038 A | 8/2000 | Michelson |
| 6,132,465 A | 10/2000 | Ray et al. |
| 6,136,031 A | 10/2000 | Middleton |
| 6,139,551 A | 10/2000 | Michelson et al. |
| 6,139,579 A | 10/2000 | Steffee et al. |
| 6,143,033 A | 11/2000 | Paul et al. |
| 6,146,421 A | 11/2000 | Gordon et al. |
| 6,156,067 A | 12/2000 | Bryan et al. |
| 6,159,214 A | 12/2000 | Michelson |
| 6,162,252 A | 12/2000 | Kuras et al. |
| 6,174,311 B1 | 1/2001 | Branch et al. |
| 6,176,881 B1 | 1/2001 | Schaer et al. |
| 6,193,757 B1 | 2/2001 | Foley et al. |
| 6,224,595 B1 | 5/2001 | Michelson |
| 6,224,607 B1 | 5/2001 | Michelson |
| 6,231,609 B1 | 5/2001 | Mehdizadeh |
| 6,235,030 B1 | 5/2001 | Zucherman et al. |
| 6,261,296 B1 | 7/2001 | Aebi et al. |
| 6,264,695 B1 | 7/2001 | Stoy |
| 6,290,726 B1 | 9/2001 | Pope et al. |
| 6,296,664 B1 | 10/2001 | Middleton |
| 6,315,797 B1 | 11/2001 | Middleton |
| 6,322,567 B1 | 11/2001 | Mittelstadt et al. |
| 6,336,941 B1 | 1/2002 | Subba et al. |
| 6,348,071 B1 | 2/2002 | Steffee et al. |
| 6,368,350 B1 | 4/2002 | Erickson et al. |
| 6,368,351 B1 | 4/2002 | Glenn et al. |
| 6,375,681 B1 | 4/2002 | Truscott |
| 6,375,682 B1 | 4/2002 | Fleischmann et al. |
| 6,395,032 B1 | 5/2002 | Gauchet |
| 6,402,785 B1 | 6/2002 | Zdeblick et al. |
| 6,409,766 B1 | 6/2002 | Brett |
| 6,413,278 B1 | 7/2002 | Marchosky |
| 6,416,551 B1 | 7/2002 | Keller |
| 6,436,098 B1 | 8/2002 | Michelson |
| 6,440,139 B2 | 8/2002 | Michelson |
| 6,447,544 B1 | 9/2002 | Michelson |
| 6,478,800 B1 | 11/2002 | Fraser et al. |
| 6,517,544 B1 | 2/2003 | Michelson |
| 6,517,580 B1 | 2/2003 | Ramadan et al. |
| 6,520,967 B1 | 2/2003 | Cauthen |
| 6,520,996 B1 | 2/2003 | Manasas et al. |
| 6,527,804 B1 | 3/2003 | Gauchet et al. |
| 6,533,817 B1 | 3/2003 | Norton et al. |
| 6,537,279 B1 | 3/2003 | Michelson |
| 6,554,863 B2 | 4/2003 | Paul et al. |

(56) References Cited

U.S. PATENT DOCUMENTS

| | | |
|---|---|---|
| 6,562,047 B2 | 5/2003 | Ralph et al. |
| 6,562,074 B2 | 5/2003 | Gerbec et al. |
| 6,565,574 B2 | 5/2003 | Michelson |
| 6,582,466 B1 | 6/2003 | Gauchet |
| 6,582,468 B1 | 6/2003 | Gauchet |
| 6,592,624 B1 | 7/2003 | Fraser et al. |
| 6,599,294 B2 | 7/2003 | Fuss et al. |
| 6,607,558 B2 | 8/2003 | Kuras |
| 6,607,559 B2 | 8/2003 | Ralph et al. |
| 6,610,092 B2 | 8/2003 | Ralph et al. |
| 6,623,525 B2 | 9/2003 | Ralph et al. |
| 6,645,248 B2 | 11/2003 | Casutt |
| 6,648,895 B2 | 11/2003 | Burkus et al. |
| 6,652,533 B2 | 11/2003 | O'Neil |
| 6,660,038 B2 | 12/2003 | Boyer et al. |
| 6,666,866 B2 | 12/2003 | Martz et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,682,562 B2 | 1/2004 | Viart et al. |
| 6,689,132 B2 | 2/2004 | Biscup |
| 6,706,068 B2 | 3/2004 | Ferree |
| 6,709,439 B2 | 3/2004 | Rogers et al. |
| 6,712,819 B2 | 3/2004 | Zucherman et al. |
| 6,712,825 B2 | 3/2004 | Aebi et al. |
| 6,723,097 B2 | 4/2004 | Fraser et al. |
| 6,726,720 B2 | 4/2004 | Ross et al. |
| 6,726,721 B2 | 4/2004 | Stoy et al. |
| 6,733,532 B1 | 5/2004 | Gauchet et al. |
| 6,740,118 B2 | 5/2004 | Eisermann et al. |
| 6,740,119 B2 | 5/2004 | Ralph et al. |
| 6,755,841 B2 | 6/2004 | Fraser et al. |
| 6,764,515 B2 | 7/2004 | Ralph et al. |
| 6,770,095 B2 | 8/2004 | Grinberg et al. |
| 6,790,233 B2 | 9/2004 | Brodke et al. |
| 6,793,678 B2 | 9/2004 | Hawkins |
| 6,814,737 B2 | 11/2004 | Cauthen |
| 6,821,298 B1 | 11/2004 | Jackson |
| 6,827,740 B1 | 12/2004 | Michelson |
| 6,846,328 B2 | 1/2005 | Cauthen |
| 6,863,673 B2 | 3/2005 | Gerbec et al. |
| 6,875,213 B2 | 4/2005 | Michelson |
| 6,896,680 B2 | 5/2005 | Michelson |
| 6,899,735 B2 | 5/2005 | Coates et al. |
| 6,936,071 B1 | 8/2005 | Marnay et al. |
| 6,936,132 B2 | 8/2005 | Topolnitsky |
| 6,964,686 B2 | 11/2005 | Gordon |
| 6,966,929 B2 | 11/2005 | Mitchell |
| 6,989,011 B2 | 1/2006 | Paul et al. |
| 6,994,727 B2 | 2/2006 | Khandkar et al. |
| 7,011,684 B2 | 3/2006 | Eckman |
| 7,022,138 B2 | 4/2006 | Mashburn |
| 7,025,787 B2 | 4/2006 | Bryan et al. |
| 7,044,983 B1 | 5/2006 | Cheng |
| 7,056,344 B2 | 6/2006 | Huppert et al. |
| 7,060,073 B2 | 6/2006 | Frey et al. |
| 7,066,958 B2 | 6/2006 | Ferree |
| 7,081,120 B2 | 7/2006 | Li et al. |
| 7,083,651 B2 | 8/2006 | Diaz et al. |
| 7,087,055 B2 | 8/2006 | Lim et al. |
| 7,097,648 B1 | 8/2006 | Globerman et al. |
| 7,115,132 B2 | 10/2006 | Errico et al. |
| 7,118,580 B1 | 10/2006 | Beyersdorff et al. |
| 7,147,665 B1 | 12/2006 | Bryan et al. |
| 7,153,325 B2 | 12/2006 | Kim et al. |
| 7,179,294 B2 | 2/2007 | Eisermann et al. |
| 7,182,784 B2 | 2/2007 | Evans et al. |
| 7,198,644 B2 | 4/2007 | Schultz et al. |
| 7,207,991 B2 | 4/2007 | Michelson |
| 7,214,244 B2 | 5/2007 | Zubok et al. |
| 7,217,291 B2 | 5/2007 | Zucherman et al. |
| 7,235,082 B2 | 6/2007 | Bartish et al. |
| 7,235,103 B2 | 6/2007 | Rivin |
| 7,250,060 B2 | 7/2007 | Trieu |
| 7,255,714 B2 | 8/2007 | Malek |
| 7,261,739 B2 | 8/2007 | Ralph et al. |
| 7,267,688 B2 | 9/2007 | Ferree |
| 7,270,679 B2 | 9/2007 | Istephanous et al. |
| 7,270,682 B2 | 9/2007 | Frigg et al. |
| 7,303,583 B1 | 12/2007 | Schaer et al. |
| 7,318,839 B2 | 1/2008 | Malberg et al. |
| 7,326,250 B2 | 2/2008 | Beaurain et al. |
| 7,331,995 B2 | 2/2008 | Eisermann et al. |
| 7,429,270 B2 | 9/2008 | Baumgartner et al. |
| 7,442,211 B2 | 10/2008 | De et al. |
| 7,452,380 B2 | 11/2008 | Zubok et al. |
| 7,491,241 B2 | 2/2009 | Errico et al. |
| 7,494,508 B2 | 2/2009 | Zeegers et al. |
| 7,531,001 B2 | 5/2009 | De et al. |
| 8,303,660 B1 | 11/2012 | Abdou |
| 8,808,383 B2 | 8/2014 | Kwak et al. |
| 8,845,730 B2 | 9/2014 | De et al. |
| 9,351,846 B2 | 5/2016 | De et al. |
| 9,351,852 B2 | 5/2016 | Bao et al. |
| 2001/0016773 A1 | 8/2001 | Serhan et al. |
| 2001/0029377 A1 | 10/2001 | Aebi et al. |
| 2002/0022845 A1 | 2/2002 | Zdeblick et al. |
| 2002/0035400 A1 | 3/2002 | Bryan et al. |
| 2002/0045904 A1 | 4/2002 | Fuss et al. |
| 2002/0068936 A1 | 6/2002 | Burkus et al. |
| 2002/0091392 A1 | 7/2002 | Michelson |
| 2002/0116009 A1 | 8/2002 | Fraser et al. |
| 2002/0123753 A1 | 9/2002 | Michelson |
| 2002/0128715 A1 | 9/2002 | Bryan et al. |
| 2002/0165550 A1 | 11/2002 | Frey et al. |
| 2002/0177897 A1 | 11/2002 | Michelson |
| 2002/0198532 A1 | 12/2002 | Michelson |
| 2003/0009224 A1 | 1/2003 | Kuras |
| 2003/0023245 A1 | 1/2003 | Ralph et al. |
| 2003/0028249 A1 | 2/2003 | Baccelli et al. |
| 2003/0040746 A1 | 2/2003 | Mitchell et al. |
| 2003/0045884 A1 | 3/2003 | Robie et al. |
| 2003/0045939 A1 | 3/2003 | Casutt |
| 2003/0074076 A1 | 4/2003 | Ferree et al. |
| 2003/0083747 A1 | 5/2003 | Winterbottom et al. |
| 2003/0100951 A1 | 5/2003 | Serhan et al. |
| 2003/0125739 A1 | 7/2003 | Bagga et al. |
| 2003/0130662 A1 | 7/2003 | Michelson |
| 2003/0135277 A1 | 7/2003 | Bryan et al. |
| 2003/0139812 A1 | 7/2003 | Garcia et al. |
| 2003/0187448 A1 | 10/2003 | Michelson |
| 2003/0191536 A1 | 10/2003 | Ferree |
| 2003/0195517 A1 | 10/2003 | Michelson |
| 2003/0195631 A1 | 10/2003 | Ferree |
| 2003/0199982 A1 | 10/2003 | Bryan |
| 2003/0204261 A1 | 10/2003 | Eisermann et al. |
| 2003/0208271 A1 | 11/2003 | Kuras |
| 2003/0229358 A1 | 12/2003 | Errico et al. |
| 2003/0233145 A1 | 12/2003 | Landry et al. |
| 2003/0233155 A1 | 12/2003 | Slemmer et al. |
| 2003/0236520 A1 | 12/2003 | Lim et al. |
| 2004/0002761 A1 | 1/2004 | Rogers et al. |
| 2004/0024407 A1 | 2/2004 | Ralph et al. |
| 2004/0024410 A1 | 2/2004 | Olson et al. |
| 2004/0030391 A1 | 2/2004 | Ferree |
| 2004/0034426 A1 | 2/2004 | Errico et al. |
| 2004/0054411 A1 | 3/2004 | Kelly et al. |
| 2004/0059318 A1 | 3/2004 | Zhang et al. |
| 2004/0073307 A1 | 4/2004 | Keller |
| 2004/0073311 A1 | 4/2004 | Ferree |
| 2004/0073312 A1 | 4/2004 | Eisermann et al. |
| 2004/0093087 A1 | 5/2004 | Ferree et al. |
| 2004/0097928 A1 | 5/2004 | Zdeblick et al. |
| 2004/0098131 A1 | 5/2004 | Bryan et al. |
| 2004/0117021 A1 | 6/2004 | Biedermann et al. |
| 2004/0143270 A1 | 7/2004 | Zucherman et al. |
| 2004/0143332 A1 | 7/2004 | Krueger et al. |
| 2004/0143334 A1 | 7/2004 | Ferree |
| 2004/0167626 A1 | 8/2004 | Geremakis et al. |
| 2004/0176843 A1 | 9/2004 | Zubok et al. |
| 2004/0186569 A1 | 9/2004 | Berry |
| 2004/0215342 A1 | 10/2004 | Suddaby |
| 2004/0225295 A1 | 11/2004 | Zubok et al. |
| 2004/0225365 A1 | 11/2004 | Eisermann et al. |

(56) References Cited

U.S. PATENT DOCUMENTS

| | | |
|---|---|---|
| 2004/0236426 A1 | 11/2004 | Ralph et al. |
| 2004/0254644 A1 | 12/2004 | Taylor |
| 2005/0015094 A1 | 1/2005 | Keller |
| 2005/0015095 A1 | 1/2005 | Keller |
| 2005/0015152 A1 | 1/2005 | Sweeney |
| 2005/0021145 A1 | 1/2005 | De et al. |
| 2005/0021146 A1 | 1/2005 | De et al. |
| 2005/0027360 A1 | 2/2005 | Webb et al. |
| 2005/0038515 A1 | 2/2005 | Kunzler |
| 2005/0043800 A1 | 2/2005 | Paul et al. |
| 2005/0085917 A1 | 4/2005 | Marnay et al. |
| 2005/0107881 A1 | 5/2005 | Alleyne et al. |
| 2005/0113842 A1 | 5/2005 | Bertagnoli et al. |
| 2005/0113928 A1 | 5/2005 | Cragg et al. |
| 2005/0143824 A1 | 6/2005 | Richelsoph et al. |
| 2005/0149189 A1 | 7/2005 | Mokhtar et al. |
| 2005/0154463 A1 | 7/2005 | Trieu |
| 2005/0165408 A1 | 7/2005 | Puno et al. |
| 2005/0192586 A1 | 9/2005 | Zucherman et al. |
| 2005/0192670 A1 | 9/2005 | Zubok et al. |
| 2005/0197706 A1 | 9/2005 | Hovorka et al. |
| 2005/0216081 A1 | 9/2005 | Taylor et al. |
| 2005/0216084 A1 | 9/2005 | Fleischmann et al. |
| 2005/0234553 A1 | 10/2005 | Gordon |
| 2005/0251260 A1 | 11/2005 | Gerber et al. |
| 2005/0251261 A1 | 11/2005 | Peterman |
| 2005/0261772 A1 | 11/2005 | Filippi et al. |
| 2005/0267580 A1 | 12/2005 | Suddaby |
| 2005/0267581 A1 | 12/2005 | Marnay et al. |
| 2006/0004377 A1 | 1/2006 | Keller |
| 2006/0004453 A1 | 1/2006 | Bartish, Jr. et al. |
| 2006/0015183 A1 | 1/2006 | Gilbert et al. |
| 2006/0020342 A1 | 1/2006 | Ferree et al. |
| 2006/0025862 A1 | 2/2006 | Villiers et al. |
| 2006/0029186 A1 | 2/2006 | De et al. |
| 2006/0030857 A1 | 2/2006 | De et al. |
| 2006/0030862 A1 | 2/2006 | De et al. |
| 2006/0036325 A1 | 2/2006 | Paul et al. |
| 2006/0041313 A1 | 2/2006 | Allard et al. |
| 2006/0041314 A1 | 2/2006 | Millard |
| 2006/0052870 A1 | 3/2006 | Ferree |
| 2006/0069439 A1 | 3/2006 | Zucherman et al. |
| 2006/0142858 A1 | 6/2006 | Colleran et al. |
| 2006/0142862 A1 | 6/2006 | Diaz et al. |
| 2006/0155378 A1 | 7/2006 | Eckman |
| 2006/0167549 A1 | 7/2006 | Mathys, Jr. et al. |
| 2006/0178744 A1 | 8/2006 | De et al. |
| 2006/0178746 A1 | 8/2006 | Bartish et al. |
| 2006/0195097 A1 | 8/2006 | Evans et al. |
| 2006/0200239 A1 | 9/2006 | Rothman et al. |
| 2006/0224241 A1 | 10/2006 | Butler et al. |
| 2006/0235426 A1 | 10/2006 | Lim et al. |
| 2006/0235525 A1 | 10/2006 | Gil et al. |
| 2006/0235527 A1 | 10/2006 | Buettner-Janz et al. |
| 2006/0241641 A1 | 10/2006 | Albans et al. |
| 2006/0241766 A1 | 10/2006 | Felton et al. |
| 2006/0259144 A1 | 11/2006 | Trieu |
| 2006/0259146 A1 | 11/2006 | Navarro et al. |
| 2006/0265068 A1 | 11/2006 | Schwab |
| 2006/0293752 A1 | 12/2006 | Moumene et al. |
| 2006/0293754 A1 | 12/2006 | Devilliers et al. |
| 2007/0010826 A1 | 1/2007 | Rhoda et al. |
| 2007/0021837 A1 | 1/2007 | Ashman |
| 2007/0032875 A1 | 2/2007 | Blacklock et al. |
| 2007/0061011 A1 | 3/2007 | De et al. |
| 2007/0067035 A1 | 3/2007 | Falahee |
| 2007/0067036 A1 | 3/2007 | Hudgins et al. |
| 2007/0073398 A1 | 3/2007 | Fabian et al. |
| 2007/0093898 A1 | 4/2007 | Schwab et al. |
| 2007/0100453 A1 | 5/2007 | Parsons et al. |
| 2007/0100454 A1 | 5/2007 | Burgess et al. |
| 2007/0100456 A1 | 5/2007 | Dooris et al. |
| 2007/0123903 A1 | 5/2007 | Raymond et al. |
| 2007/0123904 A1 | 5/2007 | Stad et al. |
| 2007/0135923 A1 | 6/2007 | Peterman et al. |
| 2007/0162133 A1 | 7/2007 | Doubler et al. |
| 2007/0168033 A1 | 7/2007 | Kim et al. |
| 2007/0168036 A1 | 7/2007 | Ainsworth et al. |
| 2007/0179615 A1 | 8/2007 | Heinz et al. |
| 2007/0213821 A1 | 9/2007 | Kwak et al. |
| 2007/0233077 A1 | 10/2007 | Khalili |
| 2007/0233247 A1 | 10/2007 | Schwab |
| 2007/0233248 A1 | 10/2007 | Schwab et al. |
| 2007/0233251 A1 | 10/2007 | Abdou |
| 2007/0233261 A1 | 10/2007 | Lopez et al. |
| 2007/0270970 A1 | 11/2007 | Trieu |
| 2007/0282449 A1* | 12/2007 | de Villiers ............ A61F 2/4611 623/17.15 |
| 2007/0299521 A1 | 12/2007 | Glenn et al. |
| 2008/0015698 A1 | 1/2008 | Marino et al. |
| 2008/0015701 A1 | 1/2008 | Garcia et al. |
| 2008/0021557 A1 | 1/2008 | Trieu |
| 2008/0051900 A1 | 2/2008 | De et al. |
| 2008/0051901 A1 | 2/2008 | De et al. |
| 2008/0114453 A1 | 5/2008 | Francis |
| 2008/0125864 A1 | 5/2008 | De et al. |
| 2008/0133011 A1 | 6/2008 | De et al. |
| 2008/0133014 A1 | 6/2008 | Gately et al. |
| 2008/0154301 A1 | 6/2008 | De et al. |
| 2008/0154382 A1 | 6/2008 | De et al. |
| 2008/0215155 A1 | 9/2008 | De et al. |
| 2008/0221696 A1 | 9/2008 | De et al. |
| 2008/0228274 A1 | 9/2008 | De et al. |
| 2008/0228277 A1 | 9/2008 | De et al. |
| 2008/0294259 A1 | 11/2008 | De et al. |
| 2009/0043391 A1 | 2/2009 | De et al. |
| 2009/0048674 A1 | 2/2009 | Zubok et al. |
| 2009/0048677 A1 | 2/2009 | McLeod et al. |
| 2009/0076614 A1 | 3/2009 | Arramon |
| 2009/0105833 A1 | 4/2009 | Hovda et al. |
| 2009/0105834 A1 | 4/2009 | Hovda et al. |
| 2009/0105835 A1 | 4/2009 | Hovda et al. |
| 2009/0222101 A1 | 9/2009 | De et al. |
| 2009/0276051 A1 | 11/2009 | Arramon et al. |
| 2010/0004746 A1 | 1/2010 | Arramon |
| 2010/0016972 A1 | 1/2010 | Jansen et al. |
| 2010/0016973 A1 | 1/2010 | De et al. |
| 2016/0242928 A1 | 8/2016 | Villiers et al. |
| 2016/0296339 A1 | 10/2016 | Villiers et al. |

FOREIGN PATENT DOCUMENTS

| | | |
|---|---|---|
| EP | 0333990 A3 | 5/1990 |
| EP | 0560140 A1 | 9/1993 |
| EP | 0560141 A1 | 9/1993 |
| EP | 0591712 A1 | 4/1994 |
| EP | 0820740 A1 | 1/1998 |
| EP | 1142544 A1 | 10/2001 |
| EP | 1153582 A2 | 11/2001 |
| EP | 1153582 A3 | 11/2001 |
| EP | 1250898 A1 | 10/2002 |
| EP | 1306064 A1 | 5/2003 |
| EP | 1344493 A1 | 9/2003 |
| EP | 1344506 A1 | 9/2003 |
| EP | 1344507 A1 | 9/2003 |
| EP | 1344508 A1 | 9/2003 |
| EP | 1405615 A1 | 4/2004 |
| EP | 1417940 A1 | 5/2004 |
| EP | 1570813 A1 | 9/2005 |
| FR | 2803741 A1 | 7/2001 |
| JP | S61122859 A | 6/1986 |
| JP | S63164948 A | 7/1988 |
| JP | H01136655 A | 5/1989 |
| JP | 06007391 | 1/1994 |
| JP | 2002521090 A | 7/2002 |
| JP | 2003508119 A | 3/2003 |
| WO | WO-9920209 A1 | 4/1999 |
| WO | WO-9930651 A1 | 6/1999 |
| WO | WO-0004851 A1 | 2/2000 |
| WO | WO-0035384 A1 | 6/2000 |
| WO | WO-0042954 A2 | 7/2000 |
| WO | WO-0042954 A3 | 11/2000 |
| WO | WO-0101893 A1 | 1/2001 |
| WO | WO-0115637 A1 | 3/2001 |

(56) References Cited

FOREIGN PATENT DOCUMENTS

| | | |
|---|---|---|
| WO | WO-0168003 A1 | 9/2001 |
| WO | WO-0211650 A2 | 2/2002 |
| WO | WO-0211650 A3 | 9/2003 |
| WO | WO-2004000170 A1 | 12/2003 |
| WO | WO-2004000171 A1 | 12/2003 |
| WO | WO-2004026187 A1 | 4/2004 |
| WO | WO-2004054477 A1 | 7/2004 |
| WO | WO-2005004756 A2 | 1/2005 |
| WO | WO-2005004756 A3 | 5/2005 |
| WO | WO-2005053580 A1 | 6/2005 |
| WO | WO-2005072662 A1 | 8/2005 |
| WO | WO-2005112834 A2 | 12/2005 |
| WO | WO-2005112834 A3 | 5/2006 |
| WO | WO-2006119092 A2 | 11/2006 |
| WO | WO-2006119092 A3 | 12/2006 |
| WO | WO-2007010161 A2 | 1/2007 |
| WO | WO-2007028098 A2 | 3/2007 |
| WO | WO-2007121320 A2 | 10/2007 |
| WO | WO-2007121320 A3 | 6/2008 |
| ZA | 200603171 | 9/2007 |

OTHER PUBLICATIONS

Hellier, et al., Wear Studies for Development of an Intervertebral Disc Prosthesis. Spine, vol. 17 No. 6 Supplement pp. 86-96 (1992).
International search report and written opinion dated Oct. 30, 2009 for PCT/US2009/050575.
Lee, et al. Impact Response of the Intervertebral Disc in a Finite-Element Model. Spine. 2000; 25(19):2431-2439.
Lehuec, et al. Shock Absorption in Lumber Disc Prosthesis. Journal of Spinal Disorders & Techniques. 2003; 16(4):346-351.
Notice of allowance dated Feb. 11, 2016 for U.S. Appl. No. 14/467,274.
Notice of allowance dated Aug. 8, 2014 for U.S. Appl. No. 12/504,042.
Office action dated Jan. 20, 2017 for U.S. Appl. No. 15/187,569.
Office action dated Apr. 18, 2014 for U.S. Appl. No. 12/504,042.
Office action dated Jul. 24, 2012 for U.S. Appl. No. 12/504,042.
Office action dated Jul. 29, 2013 for U.S. Appl. No. 12/504,042.
Office action dated Sep. 16, 2016 for U.S. Appl. No. 15/144,689.
Office action dated Sep. 16, 2016 for U.S. Appl. No. 15/187,569.
Office action dated Dec. 18, 2012 for U.S. Appl. No. 12/504,042.

\* cited by examiner

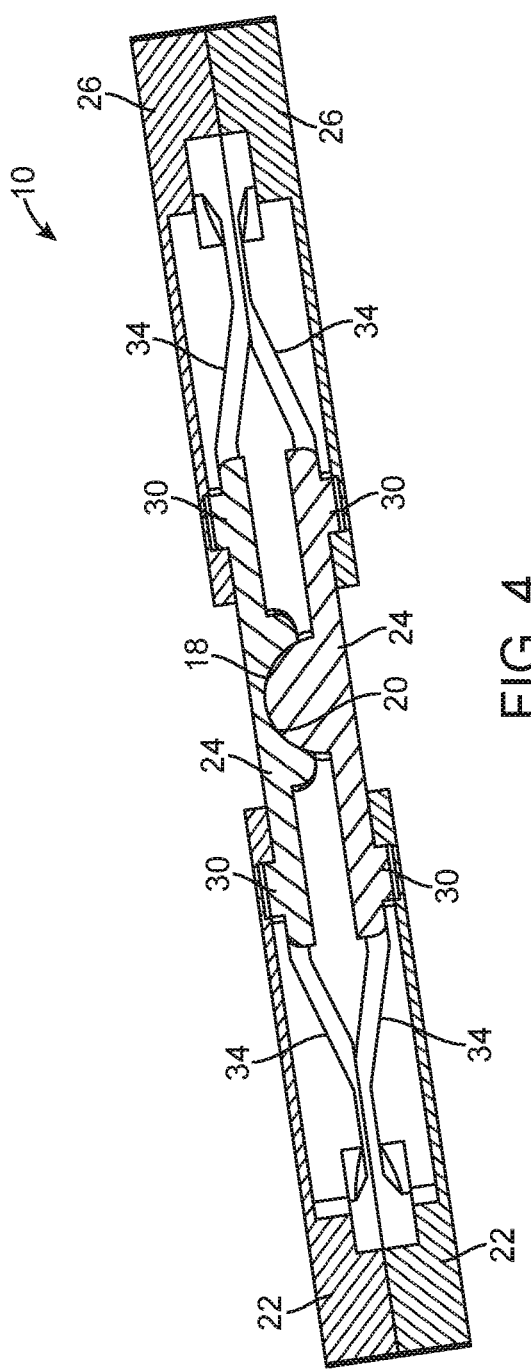
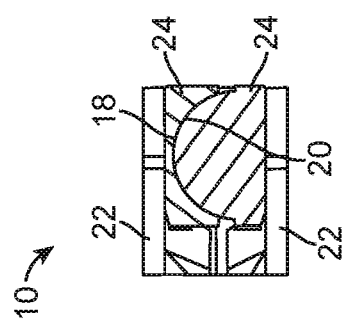

POSTERIOR PROSTHETIC INTERVERTEBRAL DISC

CROSS-REFERENCES TO RELATED APPLICATIONS

This application is a continuation of U.S. patent application Ser. No. 15/144,689, filed May 2, 2016, which is a divisional of U.S. patent application Ser. No. 14/467,274, filed Aug. 25, 2014, now U.S. Pat. No. 9,351,864, which is a divisional of U.S. patent application Ser. No. 12/504,042, filed Jul. 16, 2009, now U.S. Pat. No. 8,845,730, which claims the benefit of Provisional No. 61/081,952 filed Jul. 18, 2008, the entire contents of which are incorporated herein by reference.

BACKGROUND OF THE INVENTION

The present invention relates to medical devices and methods. More specifically, the invention relates to intervertebral prosthetic discs and methods of preserving limited motion upon removal of an intervertebral disc.

Back pain takes an enormous toll on the health and productivity of people around the world. According to the American Academy of Orthopedic Surgeons, approximately 80 percent of Americans will experience back pain at some time in their life. In the year 2000, approximately 26 million visits were made to physicians' offices due to back problems in the United States. On any one day, it is estimated that 5% of the working population in America is disabled by back pain.

One common cause of back pain is injury, degeneration and/or dysfunction of one or more intervertebral discs. Intervertebral discs are the soft tissue structures located between each of the thirty-three vertebral bones that make up the vertebral (spinal) column. Essentially, the discs allow the vertebrae to move relative to one another. The vertebral column and discs are vital anatomical structures, in that they form a central axis that supports the head and torso, allow for movement of the back, and protect the spinal cord, which passes through the vertebrae in proximity to the discs.

Discs often become damaged due to wear and tear or acute injury. For example, discs may bulge (herniate), tear, rupture, degenerate or the like. A bulging disc may press against the spinal cord or a nerve exiting the spinal cord, causing "radicular" pain (pain in one or more extremities caused by impingement of a nerve root). Degeneration or other damage to a disc may cause a loss of "disc height," meaning that the natural space between two vertebrae decreases. Decreased disc height may cause a disc to bulge, facet loads to increase, two vertebrae to rub together in an unnatural way and/or increased pressure on certain parts of the vertebrae and/or nerve roots, thus causing pain. In general, chronic and acute damage to intervertebral discs is a common source of back related pain and loss of mobility.

When one or more damaged intervertebral disc cause a patient pain and discomfort, surgery is often required. Traditionally, surgical procedures for treating intervertebral discs have involved discectomy (partial or total removal of a disc), with or without interbody fusion of the two vertebrae adjacent to the disc. When the disc is partially or completely removed, it is necessary to replace the excised disc material with natural bone or artificial support structures to prevent direct contact between hard bony surfaces of adjacent vertebrae. Oftentimes, pins, rods, screws, cages and/or the like are inserted between the vertebrae to act as support structures to hold the vertebrae and any graft material in place while the bones permanently fuse together.

A more recent alternative to traditional fusion is total disc replacement or TDR. TDR provides the ability to treat disc related pain without fusion provided by bridging bone, by using a movable, implantable, artificial intervertebral disc (or "disc prosthesis") between two vertebrae. A number of different artificial intervertebral discs are currently being developed. For example, U.S. Patent Application Publication Nos. 2005/0021146, 2005/0021145, and 2006/0025862, which are hereby incorporated by reference in their entirety, describe artificial intervertebral discs with mobile bearing designs. Other examples of intervertebral disc prostheses are the LINK® SB Charite disc (provided by DePuy Spine, Inc.) MOBIDISC® (provided by LDR Medical (www.ldrmedical.fr)), the BRYAN Cervical Disc (provided by Medtronic Sofamor Danek, Inc.), the PRODISC® or PRODISC-C® (from Synthes Stratec, Inc.), the PCM disc (provided by Cervitech, Inc.), and the MAVERICK® disc (provided by Medtronic Sofomor Danek).

A potential drawback of these known disc designs is that the prosthetic disc must be inserted from the anterior side of the patient. The anterior approach can be difficult and may require a vascular surgeon as the prosthetic disc passes near important blood vessels located anterior to the spine. Other currently available intervertebral disc prostheses usually have similar drawbacks, including invasiveness of the surgery and/or surgical skill and complexity.

Another prosthetic approach has been to fuse the vertebrae, for example with transforaminal lumbar interbody fusion (TLIF) surgery or posterior lumbar interbody fusion (PLIF) surgery. These procedures allow the surgery to be performed from the posterior without passing through the abdominal cavity and the associated drawbacks. The TLIF or PLIF approaches involve passing through a much smaller space than an anterior approach and generally require at least partial removal of one or more facet joints to provide enough space for access to the disc space. It is this limitation on space that has until now prevented the design of a successful artificial disc for delivery by a TLIF or PLIF approach.

Therefore, a need exists for an improved disc for preserving motion and maintaining disc spacing between two vertebrae after removal of an intervertebral disc which can be delivered by a TLIF or PLIF approach. Ideally, such improved disc would be introduced in a small configuration and expanded in vivo to a larger configuration.

BRIEF SUMMARY OF THE INVENTION

Embodiments of the present invention provide a prosthetic intervertebral disc which is implanted from a PLIF or TLIF approach and is deployed from a small insertion configuration to a larger deployed configuration in vivo.

In accordance with one aspect of the invention, a prosthetic intervertebral disc includes first and second end plates sized and shaped to fit within an intervertebral space, each end plate having a vertebral contacting surface and an inner surface and a first bearing surface on an inner surface of the first end plate and a second bearing surface on an inner surface of the second end plate. The first and second bearing surfaces are arranged to allow articulation and rotation between the first and second plates. The first and second plates are each formed of first, second and third parts having a first configuration in which the parts are axially aligned to a second configuration in which the parts are axially unaligned with each other. The first and second plates are deployed in situ from the first configuration to the second configuration by both rotation and sliding of the parts over one another. The deployment from the first configuration to the second configuration increases a height of the disc.

In accordance with another embodiment of the invention, a prosthetic intervertebral disc includes first and second end plates sized and shaped to fit within an intervertebral space, each end plate having a vertebral contacting surface and an inner surface, a first bearing surface on an inner surface of the first end plate and a second bearing surface on an inner surface of the second end plate, the first and second bearing surfaces opposed to one another, and a mobile core configured to be received between the first and second bearing surfaces and arranged to allow articulation and rotation between the first and second plates. The first and second plates are each formed of first, second and third parts having a first configuration in which the parts are axially aligned and a second configuration in which the parts are axially unaligned with each other. A track is formed in the first and second end plates. The track is configured to allow the mobile core to move from a first position outside of the bearing surfaces to a position between the bearing surfaces, wherein the movement of the mobile core from the first position to the second position increases a height of the disc.

In accordance with a further aspect of the invention, a method of deploying a prosthetic intervertebral disc comprises the steps of: providing a prosthetic intervertebral disc having first and second end plates each having a vertebral contacting surface and an inner surface, a first bearing surface on an inner surface of the first end plate and a second bearing surface on an inner surface of the second end plate, the first and second bearing surfaces arranged to allow articulation and rotation between the first and second plates, wherein the first and second plates are each formed of first, second and third parts; inserting the intervertebral disc between two vertebrae in a configuration in which the first, second and third parts of each of the plates are axially aligned; and deploying the first and second plates in situ from the first configuration to a second configuration in which the parts are axially unaligned with each other by both rotation and sliding of the parts over one another, wherein the deployment from the first configuration to the second configuration increases a height of the disc.

In accordance with an additional aspect of the invention, a method of deploying a prosthetic intervertebral disc includes the steps of: providing a prosthetic intervertebral disc comprising first and second end plates and a mobile core arranged to allow articulation and rotation between the first and second plates, wherein the first and second plates are each formed of first, second and third parts; inserting the intervertebral disc between two vertebrae in a configuration in which the first, second and third parts of each of the plates are substantially axially aligned; deploying the first and second plates in situ from the first configuration to a second configuration in which the parts are axially unaligned with each other; and moving the mobile core along a track between the end plates, wherein the movement of the mobile core from the first position to the second position increases a height of the disc.

BRIEF DESCRIPTION OF THE DRAWINGS

FIG. 4 is a side cross sectional view of the disc of FIG. 1 taken along the line 4-4 of FIG. 3;
FIG. 5 is a cross sectional view of the disc of FIG. 1 taken along the line 5-5 of FIG. 2.

DETAILED DESCRIPTION OF THE INVENTION

The present invention provides an implanted intervertebral disc assembly which both restores motion and can be implanted from the back of the patient, thereby decreasing the invasiveness of the procedure. The posterior approach provides for a smaller posterior surgical incision and avoids important blood vessels located anterior to the spine particularly for lumbar disc replacements. The intervertebral discs described herein are designed to be suitable for either a PLIF or TLIF approach to the spine. These approaches require insertion of a device with a small insertion profile which can be expanded or assembled in vivo into a complete disc assembly.

PLIF stands for Posterior Lumbar Interbody Fusion. In the PLIF approach to the spine, the vertebrae are reached through an incision in the patient's back (posterior). The PLIF procedure involves forming a 3-6 inch incision in the patient's back and retracting the spinal muscles to allow access to the vertebral disc. The surgeon then carefully removes the lamina (laminectomy) to be able to see and access the nerve roots. The facet joints, which lie directly over the nerve roots, may be trimmed to allow more room for the nerve roots. Depending on the amount of space available, ¼ to ½ of the facets may be removed. The surgeon then removes some or all of the affected disc and surrounding tissue. Once the disc space is prepared, hardware, such as an intervertebral disc, is inserted into the disc space. The space available for insertion of the intervertebral disc can vary depending on the patient, but generally the opening has a width and height of about 1 cm which with distraction can form a slightly larger opening.

TLIF stands for Transforaminal Lumbar Interbody Fusion. The TLIF has recently gained popularity as a surgical access to the lumbar spine and provides some potential advantages over the PLIF approach. The TLIF technique involves approaching the spine in a similar manner as the PLIF approach but more from the side of the spinal canal through a midline incision in the patient's back. This approach greatly reduces the amount of surgical muscle dissection and minimizes the nerve manipulation required to access the vertebrae, discs and nerves. The TLIF approach is generally less traumatic to the spine, is safer for the nerves, and allows for minimal access. However, the TLIF involves the removal of at least one and possibly both facets.

Figure 1:
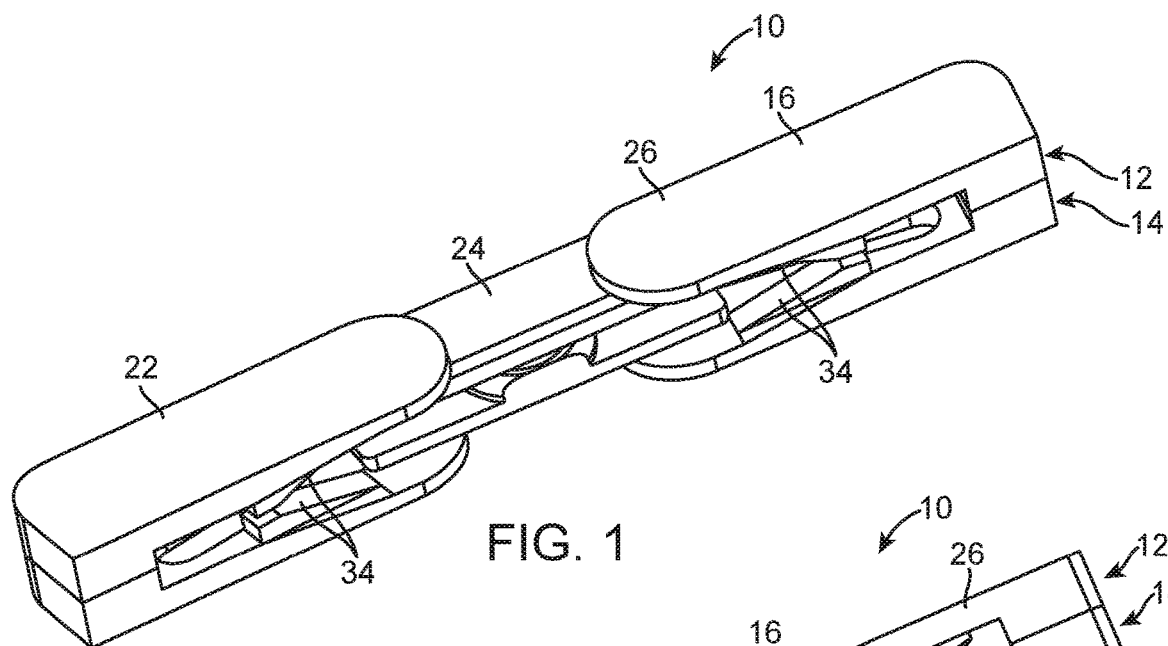
FIG. 1 is a perspective view of a posterior prosthetic intervertebral disc in a narrow insertion configuration.

FIG. 1 illustrates a prosthetic intervertebral disc 10 formed of first and second end plates 12, 14 sized and shaped to fit within an intervertebral space. Each plate 12, 14 has a vertebral contacting outer surface 16 and an inner surface carrying first and second bearing surfaces 18, 20 (shown in FIGS. 4 and 5). The first bearing surface 18 in the embodiment of FIG. 1 is a concave bearing surface while the second bearing surface 20 is a mating convex bearing surface. Together the bearing surfaces 18, 20 form a ball and socket joint arranged to allow articulation and rotation between the first and second plates 12, 14.

Figure 6:
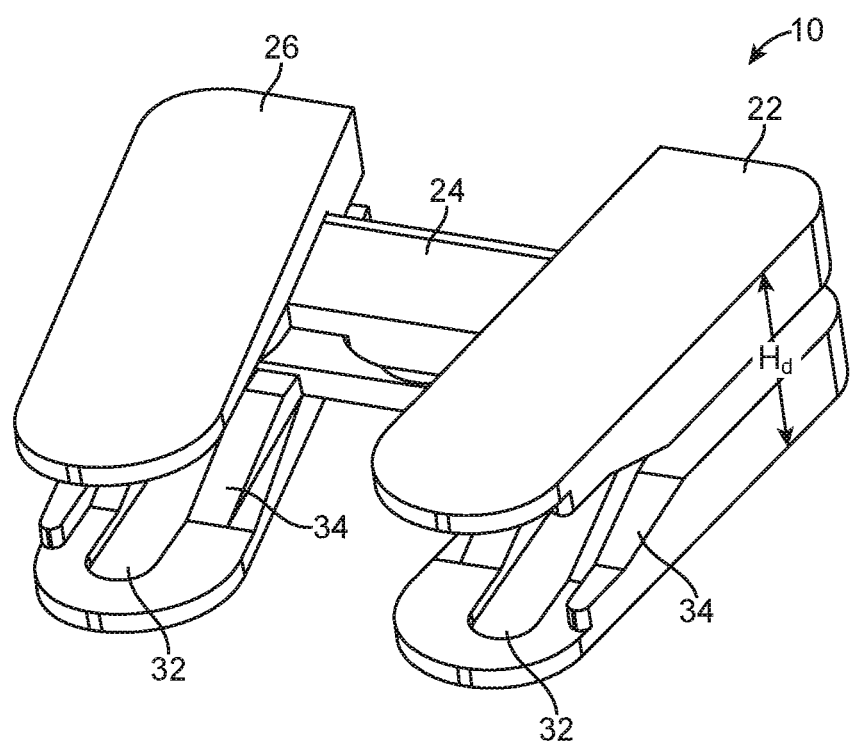
FIG. 6 is a perspective view of the disc of FIG. 1 is an expanded deployed configuration.
Figure 7:
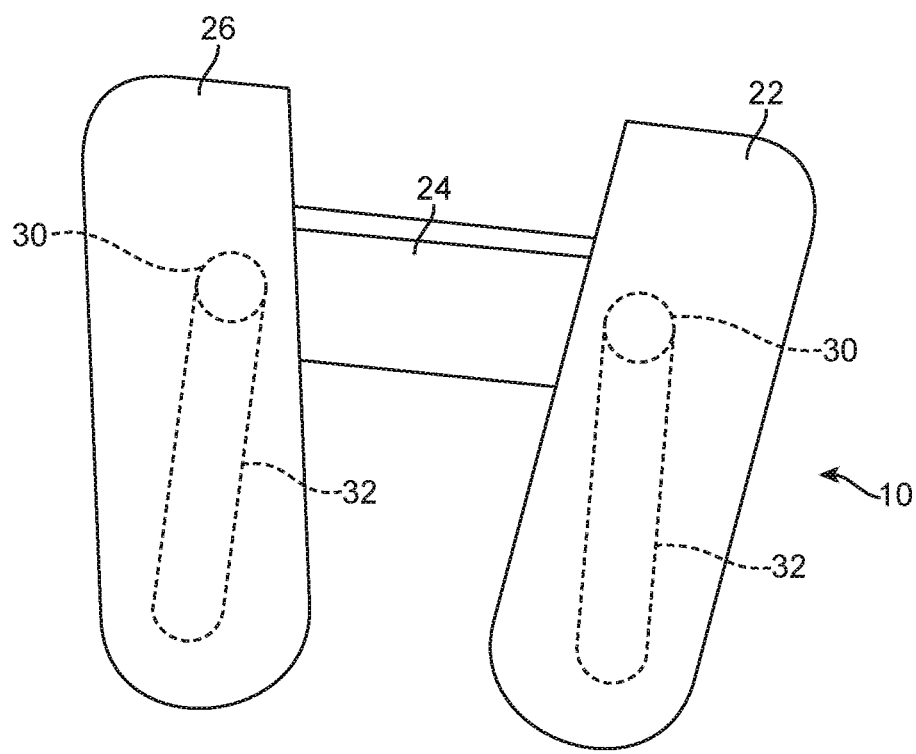
FIG. 7 is a top view of the deployed disc of FIG. 6.

The first and second plates 12, 14 are each formed of first, second and third parts 22, 24, 26. The three parts 22, 24, 26 have a first configuration, shown in FIG. 1 in which the parts are axially aligned to form a low profile device appropriate for insertion through the small opening available in the TLIF or PLIF approaches described above. Preferably, the undeployed configuration of FIG. 1 has a height less than about 10 mm and a width less than about 12 mm. The three parts 22, 24, 26 of both of the plates 12, 14 rotate and translate with respect to one another in situ to a second configuration or a deployed configuration in which the parts are axially unaligned with each other. In the deployed configuration, as shown in FIGS. 6 and 7, the three parts form a substantially H-shaped configuration which provides a maximum coverage of the vertebral end plates for a minimum of insertion profile. As the three parts 22, 24, 26 translate with respect to one another to the deployed configuration a height of the disc is increased in a manner which will be described in detail below.

The bone integration surfaces 16 of the disc 10 have been shown as flat surfaces for ease of illustration. The outer vertebral body contacting surface 16 may take on any of the configurations known in the art. Oftentimes, the outer surfaces 16 will include one or more surface features and/or materials to enhance attachment of the disc 10 to vertebral bone. For example, the outer surfaces 16 may be machined to have serrations, teeth or other surface features for promoting adhesion of the plates 12, 14 to a vertebra. In one embodiment, serrations are provided on the outer surfaces 16. The serrations can be pyramid shaped serrations extending in mutually orthogonal directions, but other geometries of serrations or other features including teeth, grooves, ridges, pins, barbs and combinations thereof would also be useful. When the bone integration structures are ridges, teeth, barbs or similar structures, they may be angled to ease insertion and prevent migration. The outer surfaces may include other fixation means inserted after deployment of the disc 10, including one or more fins, pins, or screws. In one embodiment, one or more fins are provided on the last of the three parts to enter the disc space. Optionally, additional fins may be provided that are inserted after the disc is positioned by sliding the fin(s) into one or more slots in the endplates.

The outer surfaces 16 may be provided with a rough microfinish formed by blasting with aluminum oxide microparticles or the like to improve bone integration. In some embodiments, the outer surface 16 may also be titanium plasma sprayed or HA coated to further enhance attachment of the outer surface to vertebral bone.

Figure 3:
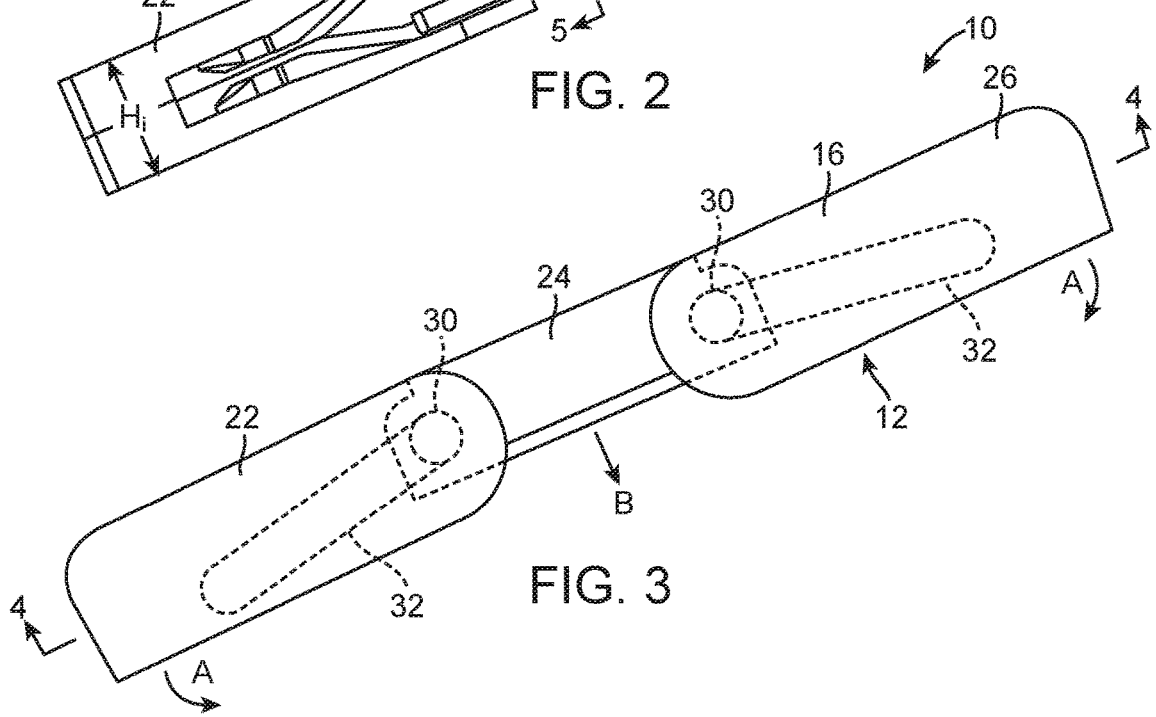
FIG. 3 is a top view of the disc of FIG. 1.

The disc 10 may be deployed with the aid of various instruments including one or more distracters, sizing guides, placement instruments and deployment instruments. The deployment instruments can be fixed to the ends of the disc 10 in the insertion configuration shown in FIG. 1 by a connection means, such as a quick connect or a threaded coupling. The placement and deployment instruments generally include at least two instruments with one instrument inserted through each of the two openings formed at the posterior side of the disc space on either side of the spine. Referring now to FIG. 3, the sequence of deployment of the disc 10 includes rotation of the first and third parts 22, 26 with respect to the second part 24 in the direction of the arrows A, followed by sliding of the second part 24 along first and third parts in the direction of the arrow B to form the deployed configuration shown in FIGS. 6 and 7.

Figure 2:
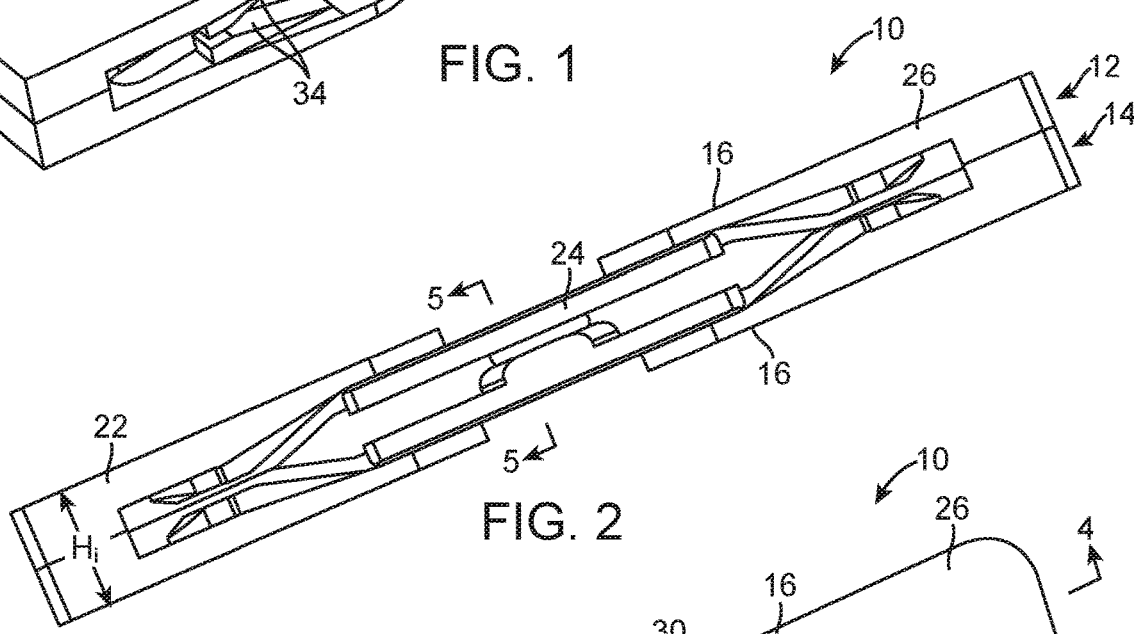
FIG. 2 is a side view of the disc of FIG. 1.

The disc 10 includes cylindrical pegs 30 on opposite ends of the second parts 24 which fit into channels 32 on the first and third parts 22, 26 to allow first rotation and then translation of the second part along the first and third parts. The rotation of the disc 10 from the substantially linear arrangement of FIGS. 1-3 to a substantially U-shaped arrangement (not shown) can be caused by contact of a leading end of the inserted disc with an annulus of the natural disc. The U-shaped configuration is then converted to the final H-shaped configuration by pulling the second part 24 posteriorly in the direction of the arrow B. The sliding of the second or center part 24 along the channels 32 causes the disc space to be distracted, i.e. the height of the disc increases from an initial height $H_i$, shown in FIG. 2 to a deployed height $H_d$, shown in FIG. 6. This distraction or separation of the end plates is provided by ramps 34 which lie along each side of the channel 32 in the first and third parts 22, 26. The deployed height $H_d$ is preferably between 1.3 and 2 times the initial height $H_i$. In one example, the deployed height $H_d$ is about 1.5 times the initial height $H_i$ and provides a final deployed disc configuration shown in FIG. 6 which is significantly higher than the height of the access opening provided by the posterior PLIF or TLIF approach.

Another embodiment of a posterior prosthetic intervertebral disc 100 is shown in FIGS. 8-12. The prosthetic disc 100 includes first and second end plates 112, 114 sized and shaped to fit within an intervertebral space, each end plate having a vertebral contacting surface 116 and an opposite inner surface including a bearing surface 118. The disc 100 includes a mobile core 120 which in a deployed configuration is positioned between the opposing bearing surfaces 118 to provide a mobile core articulating disc design. As in the embodiment of FIG. 1, each of the plates 12, 114 are formed of first, second and third parts 122, 124, 126. The three parts of the plates have a first configuration for insertion of the disc 100 through a small posterior keyhole into the disc space. In the first configuration (not shown) the three parts 122, 124, 126 are substantially axially aligned. The after insertion, the three parts 122, 124, 126 are rotated by pivoting on interconnecting posts 130 to a second configuration in which the parts are axially unaligned with each other and arranged with the first and third parts 122, 126 at an angle of about 20-90 degrees with respect to one another, preferably about 70-85 degrees.

Figure 8:
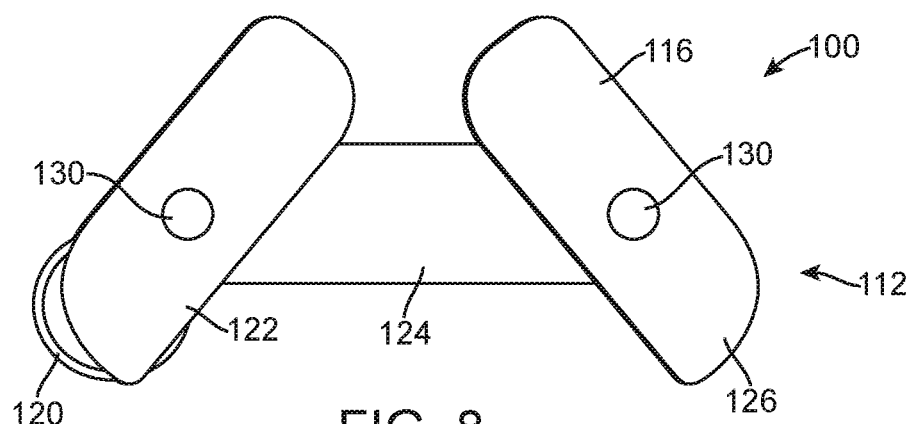
FIG. 8 is a top view of an alternative embodiment of a posterior prosthetic intervertebral disc in a partially deployed configuration.
Figure 9:
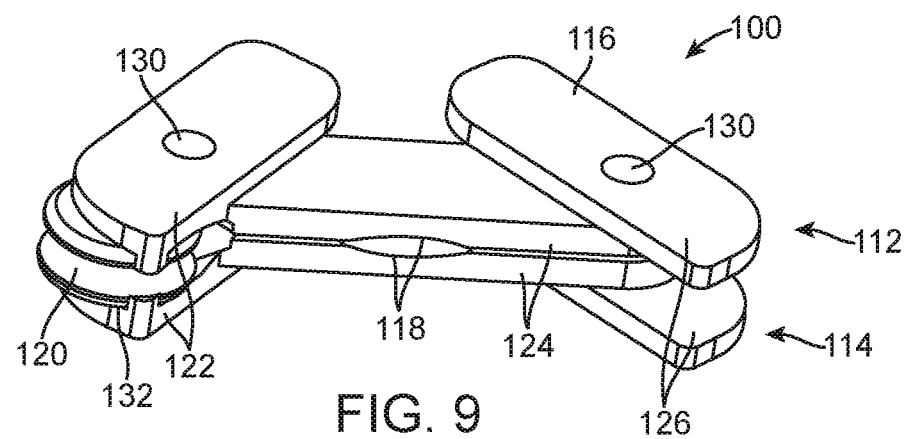
FIG. 9 is a perspective view of the disc of FIG. 8.
Figure 10:
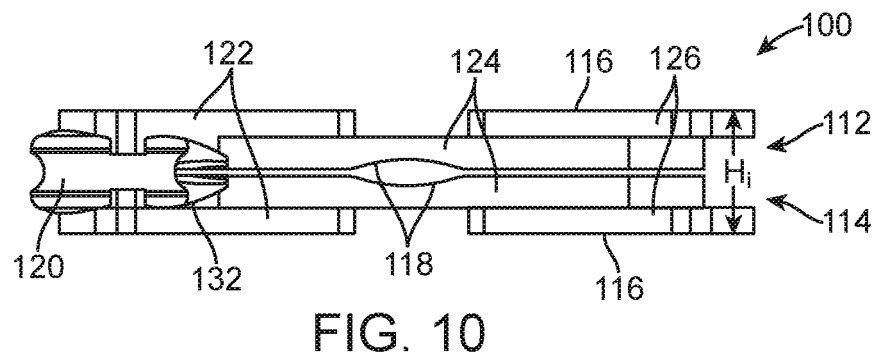
FIG. 10 is a side view of the disc of FIG. 8.
Figure 11:
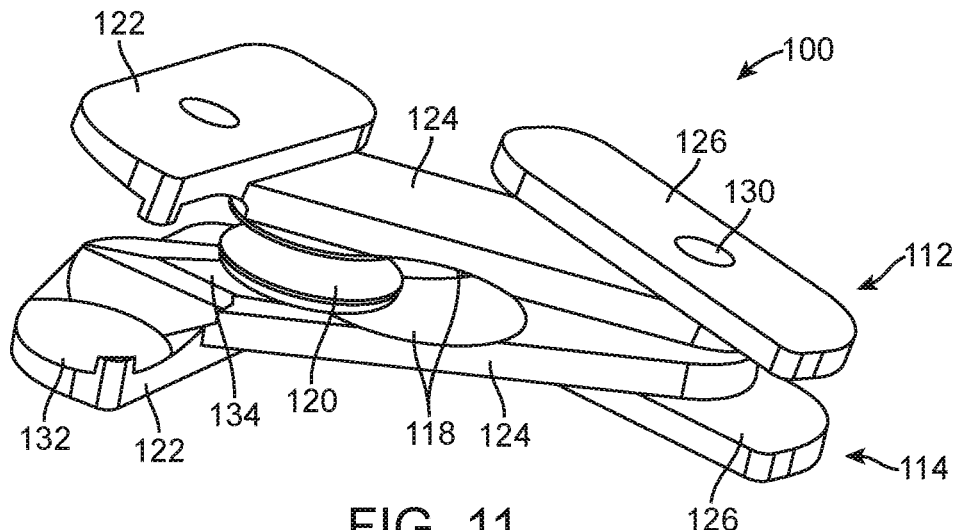
FIG. 11 is a perspective view of the disc of FIG. 8 with the core moving along a track from the position of FIG. 8 to the fully deployed position of FIG. 12.
Figure 12:
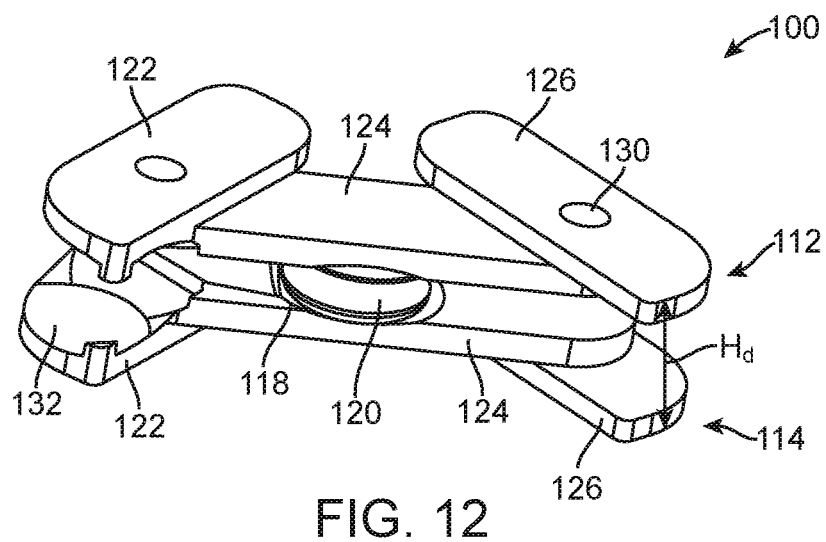
FIG. 12 is a perspective view of the disc of FIG. 8 with the core in a fully deployed position.

The mobile core 120 includes opposite convex bearing surfaces arranged to be received between the first and second bearing surfaces 118 of the plates to allow articulation, rotation and some translation between the first and second plates. As shown in FIGS. 8-10, for insertion of the disc 100 into the disc space, the core 120 is positioned in a seat 132 formed between the first parts 122 at one end of the first parts. After insertion of the disc 100 into the disc space, the core 120 is advanced along a track 134, shown in FIG. 11 from the seat 132 to a final deployed position between the bearing surfaces 118 of the plates. FIG. 12 shows the core 120 seated between the bearing surfaces 118. The bearing surfaces 118 may include one or more core retaining features, such as a retaining ring or other peripheral retaining features. As can be seen in FIG. 11, the movement of the mobile core 130 from the first position in the seat 132 to the second position between the bearing surfaces 118 distracts the plates 112, 114 away from one another and increases a height of the disc 100 from an initial height $H_i$, shown in FIG. 10 to a deployed height $H_d$ shown in FIG. 12.

The procedure for replacing a natural intervertebral disc with the artificial intervertebral discs 10, 100 includes using a PLIF or TLIF approach to the spine, by forming a 3-6 inch incision in the patient's back and retracting the spinal muscles to allow access to the vertebral disc. The surgeon then carefully removes the lamina (laminectomy) to be able to see and access the nerve roots. The disc space is then entered through a preexisting opening or through an opening formed by cutting away a portion of or an entire one or more facet. Those skilled in the art will understand the procedure of preparing the disc space and implanting the disc which is summarized herein. A far posterio-lateral minimally invasive approach can be used so as to allow for the minimum of facet removal such that the facet joints remain substantially intact. The surgeon then removes some or all of the affected disc and surrounding tissue. Once the disc space is prepared the intervertebral disc is inserted into the disc space in the insertion configuration in which the first, second and third parts are aligned. The space available for insertion of the intervertebral disc can vary depending on the patient, but generally the opening has a width and height of about 1 cm which with distraction can form a slightly larger opening, i.e. about 1 cm by 1.2 cm. The deployment of the discs 10, 100 can be performed through a single posterior opening, or preferably, through two posterior openings to allow the surgeon better access to deploy the disc. In one embodiment, one of the two openings is used for insertion of the disc while the other opening is used for a distraction instrument and/or other deployment instruments.

The upper and lower plates 12, 14, 112, 114 may be constructed from any suitable metal, alloy or combination of metals or alloys, such as but not limited to cobalt chrome alloys, titanium (such as grade 5 titanium), titanium based alloys, tantalum, nickel titanium alloys, stainless steel, and/or the like. They may also be formed of ceramics, biologically compatible polymers including PEEK, UHMWPE, PLA or fiber reinforced polymers. The plates 12, 14, 112, 114 may be formed of a one piece construction or may be formed of more than one piece, such as different materials coupled together.

The core 130 can be made of low friction materials, such as titanium, titanium nitrides, other titanium based alloys, tantalum, nickel titanium alloys, stainless steel, cobalt chrome alloys, ceramics, or biologically compatible polymer materials including PEEK, UHMWPE, PLA or fiber reinforced polymers. High friction coating materials can also be used.

Different materials may be used for different parts of the disc 10 to optimize imaging characteristics. PEEK plates may also be coated with titanium plasma spray or provided with titanium screens for improved bone integration. Other materials and coatings can also be used such as titanium coated with titanium nitride, aluminum oxide blasting, HA (hydroxylapatite) coating, micro HA coating, and/or bone integration promoting coatings. Any other suitable metals or combinations of metals may be used as well as ceramic or polymer materials, and combinations thereof. Any suitable technique may be used to couple materials together, such as snap fitting, slip fitting, lamination, interference fitting, use of adhesives, welding and the like.

Although the present invention has been described as having a ball in socket design (disc 10) or a mobile core design (disc 100), the articulation surfaces may be varied to take on any of the different articulation designs known in the art. For example, the disc 10 may use a mobile bearing design in place of the ball and socket articulation. In one alternative embodiment of the invention non-symmetrically shaped bearing surfaces are used to tailor the articulation of the disc to the anatomy. In one example, the bearing surfaces are arranged to allow a maximum of 12 degrees of motion in flexion, a maximum of 8 degrees in extension and a maximum of 8 degrees in each direction of lateral bending. This configuration is useful particularly in the lumbar spine where the average range of motion of the various segments is larger in flexion that in extension or lateral bending.

Although the core 130 of FIG. 8 has been shown as circular in cross section with spherically shaped bearing surfaces, other shapes may be used including oval, elliptical, or kidney bean shaped. The circular shaped core does not limit rotational motion between the plates. The non-circular shaped cores can be used to limit rotational motion between the upper and lower plates 112, 113. When the core 130 is formed of a polymer such as PEEK which is invisible under radiographic imaging, it may be desirable to have a radiographic marker imbedded within the core.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. A method of deploying an implant in a spine of a patient, the method comprising:

providing the implant having first and second interconnected elongated articulating endplates, each of the elongated articulating endplates having two parts interconnected through a height-adjustable member including articulating bearing surface, wherein the first and second interconnected elongated endplates articulate relative to each other via the interconnected bearing surfaces of the first and second interconnected elongated articulating endplates, each of the parts having a vertebral contacting outer surface, each of the first and second interconnected elongated articulating endplates having a length, a width and a height, wherein the length is longer than the width and the height, and wherein each of the parts and the height-adjustable members having an axis extending along a length thereof, and wherein the parts of each of the first and second elongated articulated endplates are each pivotably and slidably interconnected to the height-adjustable members to pivot and slide relative to the height-adjustable members between an axially aligned insertion configuration and an axially unaligned deployed configuration;

arranging the parts of the first and second interconnected elongated articulating endplates relative to the height-adjustable members with their axes substantially aligned in the insertion configuration;

inserting the implant having the first and second interconnected elongated articulating endplates into a natural disc space between two vertebrae in the insertion configuration in which the implant has a first width;

deploying the implant having the first and second interconnected elongated articulating endplates inside the natural disc space by pivoting the parts of the first and second interconnected elongated articulating endplates relative to the height-adjustable members from the axially aligned insertion configuration to the axially unaligned deployed configuration in which the axes of the parts of the first and second interconnected elongated articulating endplates are axially unaligned with the axes of the height-adjustable members and the implant has a second width greater than the first width, wherein the implant in the deployed configuration has the vertebral contacting outer surfaces of the first elongated endplate in contact with one of the two vertebrae and the vertebral contacting outer surfaces of the second elongated endplate in contact with the other of the two vertebrae; and increasing a height of the implant having the first and second interconnected elongated articulating endplates by expanding the entire implant, via slidably adjusting the height-adjustable members relative to the parts of the first and second interconnected articulating endplates, from an initial height to a deployed height while the implant is inside the disc space, wherein the initial height and the deployed height are measured at a same location of the implant between the vertebral contacting outer surfaces of the first elongated endplate and the vertebral contacting outer surfaces of the second elongated endplate.

2. The method of claim 1, wherein the parts of the first and second interconnected elongated articulating endplates are each interconnected to the height-adjustable members through a pivot.

3. The method of claim 2, wherein the implant comprises a coupling at an end thereof for connecting to a deployment instrument.

4. The method of claim 1, wherein the step of inserting is performed by a PLIF approach in the spine.

5. The method of claim 1, wherein the step of inserting is performed by a TLIF approach in the spine.

6. The method of claim 1, wherein the outer vertebral contacting surfaces of the first and second interconnected elongated articulating endplates comprise teeth, grooves or ridges.

7. The method of claim 6, wherein the teeth, grooves or ridges are angled to ease insertion and prevent migration.

8. The method of claim 1, wherein the implant is inserted by a deployment instrument fixed to an ends of the implant in the axially aligned insertion configuration.

9. The method of claim 3, further comprising attaching the deployment instrument to the coupling and inserting the implant with the deployment instrument.

10. The method of claim 1, wherein the step of deploying the implant from the axially aligned insertion configuration to the axially unaligned deployed configuration is caused by contact of a leading end of the implant with an annulus of the natural disc.

11. The method of claim 1, wherein the step of increasing the height of the implant is performed during the deploying step.

12. The method of claim 1, wherein the step of increasing the height of the implant is performed after the deploying step.

13. The method of claim 1, wherein the inserting step and the deploying step are performed through a single posterior opening into the disc space.

14. The method of claim 1, wherein the deployed height is at least 1.5 times the initial height in the insertion configuration.

15. A method of deploying an implant in a spine of a patient, the method comprising:

providing the implant having first and second interconnected elongated articulating endplates, each of the elongated articulating endplates having two parts interconnected through a height-adjustable member including articulating bearing surface, wherein the first and second interconnected elongated endplates articulate relative to each other via the interconnected bearing surfaces of the first and second interconnected elongated articulating endplates, each of the parts having a vertebral contacting outer surface, each of the first and second interconnected elongated articulating endplates having a length, a width and a height, wherein the length is longer than the width and the height, and wherein each of the parts and the height-adjustable members having an axis extending along a length thereof, and wherein the parts of each of the first and second elongated articulated endplates are each pivotably and slidably interconnected to the height-adjustable members to pivot and slide relative to the height-adjustable member between an axially aligned insertion configuration and an axially unaligned deployed configuration;

arranging the parts of the first and second interconnected elongated articulating endplates relative to the height-adjustable members with their axes substantially aligned in the insertion configuration;

inserting the implant having the first and second interconnected elongated articulating endplates into a natural disc space between two vertebrae in the insertion configuration in which the implant has a first width;

deploying the implant having the first and second interconnected elongated articulating endplates inside the natural disc space by pivoting the parts of the first and second interconnected elongated articulating endplates relative to the height-adjustable members from the axially aligned insertion configuration to the axially unaligned deployed configuration in which the axes of the parts of the first and second interconnected elongated articulating endplates are axially unaligned with the axes of the height-adjustable members and the implant has a second width greater than the first width, wherein the implant in the deployed configuration has the vertebral contacting outer surfaces of the first elongated endplate in contact with one of the two vertebrae and the vertebral contacting outer surfaces of the second elongated endplate in contact with the other of the two vertebrae; and increasing a height of the implant having the first and second interconnected elongated articulating endplates by expanding the entire implant, via slidably adjusting the height-adjustable members relative to the parts of the first and second interconnected articulating endplates, from an initial height to a deployed height measured at a same location of the implant between the vertebral contacting outer surfaces of the first elongated endplate and the vertebral contacting outer surfaces of the second elongated endplate, wherein said deploying and increasing a height of the implant comprises pivoting and sliding of the parts of said first and second interconnected elongated articulating endplates about pivots, said pivots extending primarily from the height-adjustable members in a direction perpendicular to said vertebral contacting outer surfaces.

16. The method of claim 15, wherein the parts of the second elongated articulating endplate are interconnected to the corresponding height-adjustable member through two of the pivots extending therefrom.

17. The method of claim 15, wherein the step of inserting is performed by a PLIF approach in the spine.

18. The method of claim 15, wherein the step of inserting is performed by a TLIF approach in the spine.

19. The method of claim 15, wherein the outer vertebral contacting surfaces of the parts of the first and second elongated articulating endplates comprise teeth, grooves or ridges.

20. The method of claim 15, wherein the implant is inserted by a deployment instrument fixed to an end of the implant in the axially aligned insertion configuration.

21. The method of claim 16, further comprising attaching a deployment instrument to a coupling at an end of the implant and inserting the implant in the natural disc space with the deployment instrument.

22. The method of claim 15, wherein the step of deploying the implant from the axially aligned insertion configuration to the axially unaligned deployed configuration is caused by contact of a leading end of the implant with an annulus of the natural disc.

23. The method of claim 15, wherein the step of increasing the height of the implant is performed during the deploying step.

24. The method of claim 15, wherein the step of increasing the height of the implant is performed after the deploying step.

25. The method of claim 15, wherein the inserting step and the deploying step are performed through a single posterior opening into the natural disc space.

26. The method of claim 15, wherein the deployed height is at least 1.5 times the initial height in the insertion configuration.

27. A method of deploying an implant in a spine of a patient, the method comprising:
providing the implant comprising:
a first interconnected elongated articulating endplate having parts interconnected through a height-adjustable member including articulating bearing surface, each of the parts having a vertebral contacting outer surface, the first interconnected elongated articulating endplate having a length, a width and a height, wherein the length is longer than the width and the height, and wherein each of the parts and the height-adjustable member having an axis extending along a length thereof; and
a second interconnected elongated articulating endplate having parts interconnected through a height-adjustable member including articulating bearing surface, each of the parts of the second endplate having a vertebral contacting outer surface, and wherein each of the parts and the height-adjustable member of the second endplate having an axis extending along a length thereof;
wherein the first and second interconnected elongated endplates articulate relative to each other via the interconnected bearing surfaces of the first and second interconnected elongated articulating endplates, and
wherein the parts of the first and second elongated articulated endplates are each pivotably and slidably interconnected to the height-adjustable members to pivot and slide relative to the height-adjustable members between an axially aligned insertion configuration and an axially unaligned deployed configuration;
arranging the parts of the first and second interconnected articulating endplates relative to the height-adjustable members with their axes substantially aligned in the insertion configuration;
inserting the implant having the first and second interconnected articulating endplates into a natural disc space between two vertebrae in the insertion configuration in which the implant has a first width;
deploying the implant having the first and second interconnected articulating endplates inside the disc space by pivoting the parts of the first and second interconnected elongated articulating endplates relative to the height-adjustable members from the axially aligned insertion configuration to the axially unaligned deployed configuration in which the axes of the parts of the first and second articulating endplates are axially unaligned with the axes of the height-adjustable members and the implant has a second width greater than the first width, wherein the implant in the deployed configuration has the vertebral contacting outer surfaces of the first elongated endplate in contact with one of the two vertebrae and the vertebral contacting outer surfaces of the second elongated endplate in contact with the other of the two vertebrae; and
increasing a height of the implant having the first and second interconnected elongated articulating endplates by expanding the entire implant, via slidably adjusting the height-adjustable members relative to the parts of the first and second interconnected articulating endplates, from an initial height to a deployed height while the implant is inside the disc space, wherein the initial height and deployed height are measured at a same location of the implant between the vertebral contacting outer surfaces of the first elongated endplate and the vertebral contacting outer surfaces of the second elongated endplate, wherein said increasing comprises sliding the height-adjustable member of said first interconnected elongated articulating endplate along ramps formed in said parts of the first interconnected elongated articulating endplate and sliding the height-adjustable member of said second interconnected elongated articulating endplate along ramps formed in said parts of the second interconnected elongated articulating endplate, said sliding causing said increasing a height of the entire implant from the initial height to the deployed height.

28. The method of claim 27, wherein the parts of the first and second articulating endplates are each interconnected to the height-adjustable members through a pivot.

29. The method of claim 27, wherein the implant comprises a coupling at an end thereof for connecting to a deployment instrument.

30. The method of claim 27, wherein the step of inserting is performed by a PLIF approach in the spine.

31. The method of claim 27, wherein the step of inserting is performed by a TLIF approach in the spine.

32. The method of claim 27, wherein the outer vertebral contacting surfaces comprise teeth, grooves or ridges.

33. The method of claim 27, wherein the implant is inserted by a deployment instrument fixed to an end of the implant in the axially aligned insertion configuration.

34. The method of claim 29, further comprising attaching the deployment instrument to the coupling and inserting the implant with the deployment instrument.

35. The method of claim 27, wherein the step of deploying the implant from the axially aligned insertion configuration to the axially unaligned deployed configuration is caused by contact of a leading end of the implant with an annulus of the natural disc.

36. The method of claim 27, wherein the step of increasing the height of the implant is performed after the deploying step.

37. The method of claim 27, wherein the deployed height is at least 1.5 times the initial height in the insertion configuration.

38. A method of deploying an implant in a spine of a patient, the method comprising:
providing the implant having first and second interconnected elongated articulating endplates, each of the elongated articulating endplates having two parts interconnected through a height-adjustable member including articulating bearing surface, wherein the first and second interconnected elongated endplates articulate relative to each other via the interconnected bearing surfaces of the first and second interconnected elongated articulating endplates, each of the parts having a vertebral contacting outer surface, each of the first and second interconnected elongated articulating endplates having a length, a width and a height, wherein the length is longer than the width and the height, and wherein each of the parts and the height-adjustable members having an axis extending along a length thereof, and
wherein the parts the first and second elongated articulated endplates are each pivotably and slidably interconnected to the height-adjustable members to pivot and slide relative to the height-adjustable members between an axially aligned insertion configuration and an axially unaligned deployed configuration;
arranging the parts of the first and second interconnected elongated articulating endplates relative to the height-adjustable members with their axes substantially aligned in the insertion configuration;
connecting an end of the implant to a deployment instrument;
inserting the implant having the first and second interconnected elongated articulating endplates into a natural disc space between two vertebrae in the insertion configuration; and
contacting a leading end of the first and second interconnected elongated articulating endplates with an annulus of the natural disc to cause the parts of the implant to pivot relative to the height-adjusting members inside the disc space from the axially aligned insertion configuration to the axially unaligned deployed configuration in which the axes of the parts of the first and second elongated articulating endplates are axially unaligned with the axes of the height-adjustable members and the implant has a second width in the axially unaligned deployed configuration greater than a first width in the axially aligned insertion configuration, and wherein the implant in the deployed configuration has the vertebral contacting outer surfaces of the first elongated endplate in contact with one of the two vertebrae and the vertebral contacting outer surfaces of the second elongated endplate in contact with the other of the two vertebrae;
expanding the implant having the first and second interconnected elongated articulating endplates by increasing a height of the entire implant from an initial height to a deployed height, via slidably adjusting the height-adjustable members relative to the parts of the first and second interconnected articulating endplates, in a height direction measured at a same location of the implant between the vertebral contacting outer surfaces of the first elongated endplate and the vertebral contacting outer surfaces of the second elongated endplate while the implant is inside the disc space, wherein said increasing a height of the entire implant comprises pivoting and sliding of the parts of said first and second interconnected elongated articulating endplates about pivots, said pivots extending primarily from the height-adjustable members in a direction perpendicular to said vertebral contacting outer surfaces; and
disconnecting the deployment instrument from the implant.

39. The method of claim 38, wherein the step of increasing a height of the entire implant comprises increasing a maximum height of the implant between the vertebral contacting outer surfaces of the first elongated endplate and the vertebral contacting outer surfaces of the second elongated endplate from an initial maximum height to a deployed maximum height.

40. The method of claim 38, wherein the leading end of the implant which contacts the annulus of the natural disc to cause the implant to articulate inside the disc space has a curved portion.

41. A method of deploying an implant in a spine of a patient, the method comprising:
providing the implant comprising:
a first interconnected elongated articulating endplate having parts interconnected through a height-adjustable member including articulating bearing surface, each of the parts having a vertebral contacting outer surface, the first interconnected elongated articulating endplate having a length, a width and a height, wherein the length is longer than the width and the height, and wherein each of the parts and the height-adjustable member having an axis extending along a length thereof; and
a second interconnected elongated articulating endplate having parts interconnected through a height-adjustable member including articulating bearing surface, each of the parts of the second endplate having a vertebral contacting outer surface, and wherein each of the parts and the height-adjustable member of the second endplate having an axis extending along a length thereof;
wherein the first and second interconnected elongated endplates articulate relative to each other via the interconnected bearing surfaces of the first and second interconnected elongated articulating endplates, and
wherein the parts of the first and second elongated articulated endplates are each pivotably and slidably interconnected to the height-adjustable members to pivot and slide relative to the height-adjustable members between an axially aligned insertion configuration and an axially unaligned deployed configuration;
arranging the parts of the first and second interconnected articulating endplates relative to the height-adjustable members with their axes substantially aligned in the insertion configuration;
connecting an end of the implant to a deployment instrument;
inserting the implant having the first and second interconnected elongated articulating endplates into a natural disc space between two vertebrae in the insertion configuration; and
contacting a leading end of the first and second interconnected elongated articulating endplates with an annulus of the natural disc to cause the parts of the implant to pivot relative to the height-adjusting members inside the disc space from the axially aligned insertion configuration to the axially unaligned deployed configuration in which the axes of the parts of the first and second elongated articulating endplates are axially unaligned with the axes of the height-adjustable members and the implant has a second width in the axially unaligned deployed configuration greater than a first width in the axially aligned insertion configuration, and wherein the implant in the deployed configuration has the vertebral contacting outer surfaces of the first elongated endplate in contact with one of the two vertebrae and the vertebral contacting outer surfaces of the second elongated endplate in contact with the other of the two vertebrae;

expanding the implant having the first and second interconnected elongated articulating endplates by increasing a height of the entire implant from an initial height to a deployed height, via slidably adjusting the height-adjustable members relative to the parts of the first and second interconnected articulating endplates, in a height direction measured at a same location of the implant between the vertebral contacting outer surfaces of the first elongated endplate and the vertebral contacting outer surfaces of the second elongated endplate while the implant is inside the disc space, wherein said expanding comprises sliding the height-adjustable member of said first interconnected elongated articulating endplate along ramps formed in said parts of the first interconnected elongated articulating endplate and sliding the height-adjustable member of said second interconnected elongated articulating endplate along ramps formed in said parts of the second interconnected elongated articulating endplate, said sliding causing said expanding of the implant from the initial height to the deployed height; and disconnecting the deployment instrument from the second articulating portion.

42. The method of claim 41, wherein the step of inserting is performed by a PLIF approach.

43. The method of claim 41, wherein the leading end of the first and second elongated articulating endplates which contacts the annulus of the natural disc to cause the parts of the implant to pivot relative to the height-adjusting members inside the disc space is curved.

44. The method of claim 41, wherein the step of increasing a height of the entire implant comprises increasing a maximum height of the implant between the vertebral contacting outer surfaces of the first elongated endplate and the vertebral contacting outer surfaces of the second elongated endplate from an initial maximum height to a deployed maximum height.

45. The method of claim 41, wherein the step of increasing a height of the entire implant includes expanding substantially the entire implant via the height-adjustable members from the initial height to the deployed height.

* * * * *